US009410934B2

(12) United States Patent
Robinson et al.

(10) Patent No.: US 9,410,934 B2
(45) Date of Patent: Aug. 9, 2016

(54) NANOPARTICLE PROBES, METHODS, AND SYSTEMS FOR USE THEREOF

(75) Inventors: Amelia C Robinson, Houston, TX (US); Robert J. Pottorf, Houston, TX (US); Daniel S. Jones, St. Paul, MN (US); Sebastien L. Dreyfus, Houston, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 219 days.

(21) Appl. No.: 14/350,908

(22) PCT Filed: Jul. 5, 2012

(86) PCT No.: PCT/US2012/045574
§ 371 (c)(1),
(2), (4) Date: Apr. 10, 2014

(87) PCT Pub. No.: WO2013/062640
PCT Pub. Date: May 2, 2013

(65) Prior Publication Data
US 2014/0249053 A1    Sep. 4, 2014

Related U.S. Application Data

(60) Provisional application No. 61/549,618, filed on Oct. 20, 2011.

(51) Int. Cl.
*G01V 3/00*  (2006.01)
*G01N 33/24*  (2006.01)
(Continued)

(52) U.S. Cl.
CPC ............ *G01N 33/241* (2013.01); *C12Q 1/6888* (2013.01); *E21B 47/1015* (2013.01);
(Continued)

(58) Field of Classification Search
CPC . G01N 33/2811; G01N 33/241; G01N 33/28; G01N 2030/8854
USPC ........... 324/323–377; 435/6.1, 6.19; 977/738, 977/746, 704, 728, 800, 924
See application file for complete search history.

(56) References Cited

U.S. PATENT DOCUMENTS 4,905,761 A    3/1990  Bryant
5,635,712 A    6/1997  Scott, III et al.
(Continued)

FOREIGN PATENT DOCUMENTS

EP    2 423 712 A2    2/2012
WO    01/81914    11/2001
(Continued)

OTHER PUBLICATIONS

Head, I., et al., (2006), "Marine microorganisms make a meal of oil" *Nature Reviews Microbiology*, 4, pp. 173-182.
(Continued)

*Primary Examiner* — Patrick Assouad
*Assistant Examiner* — Sean Curtis
(74) *Attorney, Agent, or Firm* — ExxonMobil Upstream Research Company, Law Department

(57) ABSTRACT

Methods of identifying geological materials of interest comprising (i) providing a nanoprobe composition comprising one or more nanoprobes; wherein the nanoprobe includes (a) at least one tag; and (b) at least one signal generator; (ii) introducing the nanoprobes to a geological material; and (iii) detecting the presence of a signal generated by the signal generator on association of the tag with a target. Nanoprobe compositions identify geological materials, systems include such nanoprobe compositions, and methods use such nanoprobe compositions for the evaluation of geological materials.

35 Claims, 3 Drawing Sheets

(51) Int. Cl.
  *G01N 21/65* (2006.01)
  *G01N 21/64* (2006.01)
  *C12Q 1/68* (2006.01)
  *G01V 9/00* (2006.01)
  *E21B 47/10* (2012.01)
  *G01N 33/28* (2006.01)
  *G01N 21/78* (2006.01)

(52) U.S. Cl.
  CPC .......... *G01N21/643* (2013.01); *G01N 21/6489* (2013.01); *G01N 21/65* (2013.01); *G01V 9/007* (2013.01); *G01N 21/78* (2013.01); *G01N 33/24* (2013.01); *G01N 33/28* (2013.01); *G01N 2021/6432* (2013.01)

(56) References Cited

U.S. PATENT DOCUMENTS

| | | | |
|---|---|---|---|
| 8,564,296 B2* | 10/2013 | Zhdanov | G01V 3/083 324/335 |
| 2005/0274510 A1 | 12/2005 | Nguyen et al. | |
| 2006/0040286 A1* | 2/2006 | Mirkin | C12Q 1/6816 435/6.11 |
| 2008/0136420 A1* | 6/2008 | Velikhov | G01V 3/12 324/335 |
| 2009/0179649 A1 | 7/2009 | Schmidt et al. | |
| 2009/0200486 A1 | 8/2009 | Wu et al. | |
| 2009/0288820 A1* | 11/2009 | Barron | B01J 13/02 166/249 |
| 2010/0015612 A1 | 1/2010 | Pelham et al. | |
| 2010/0038079 A1 | 2/2010 | Greenway | |
| 2010/0102986 A1* | 4/2010 | Benischek | E21B 47/122 340/855.8 |
| 2010/0132450 A1 | 6/2010 | Pomerantz et al. | |
| 2010/0307745 A1 | 12/2010 | Lafitte et al. | |
| 2010/0323910 A1 | 12/2010 | Wunch et al. | |
| 2011/0086774 A1 | 4/2011 | Dunaway | |
| 2011/0300071 A1* | 12/2011 | Woodard | A61K 49/085 424/1.69 |
| 2011/0308790 A1 | 12/2011 | Strapoc et al. | |
| 2013/0338923 A1* | 12/2013 | Zhdanov | G01V 3/08 702/6 |
| 2014/0249053 A1* | 9/2014 | Robinson | G01N 21/65 506/9 |
| 2015/0012218 A1* | 1/2015 | Selman | E21B 49/005 702/9 |
| 2015/0012219 A1* | 1/2015 | Selman | E21B 49/005 702/9 |
| 2016/0003037 A1* | 1/2016 | Khalid | E21B 49/00 73/152.05 |
| 2016/0076086 A1* | 3/2016 | Vo-Dinh | C12Q 1/6825 424/490 |

FOREIGN PATENT DOCUMENTS

| | | | |
|---|---|---|---|
| WO | 03/012390 | 2/2003 | |
| WO | WO 2007070572 | * 6/2007 | .......... C12Q 1/6818 |
| WO | 2010/011402 | 1/2010 | |
| WO | WO 2010/147859 | 12/2010 | |
| WO | WO 2011/127001 | 10/2011 | |
| WO | WO 2013062640 | * 5/2013 | .......... G01N 21/65 |

OTHER PUBLICATIONS

Young, L., et al., (2005), "Metabolic biomarkers for monitoring in situ anaerobic hydrocarbon degradation", *Environmental Health Perspectives* 113 (1), pp. 62-67.

Wenger, L.M., et al. (2002), "Multiple controls on petroleum biodegradation and impact on oil quality", *SPE Reservoir Evaluation and Engineering*, 5, pp. 375-383.

Clarke, S. et al., "Bacterial and Mineral Elements in an Arctic Biofilm: A Correlative Study Using Fluoresence and Electron Microscopy," XP001552873, *Microscopy and Microanalysis* 16(2), pp. 153-165.

* cited by examiner

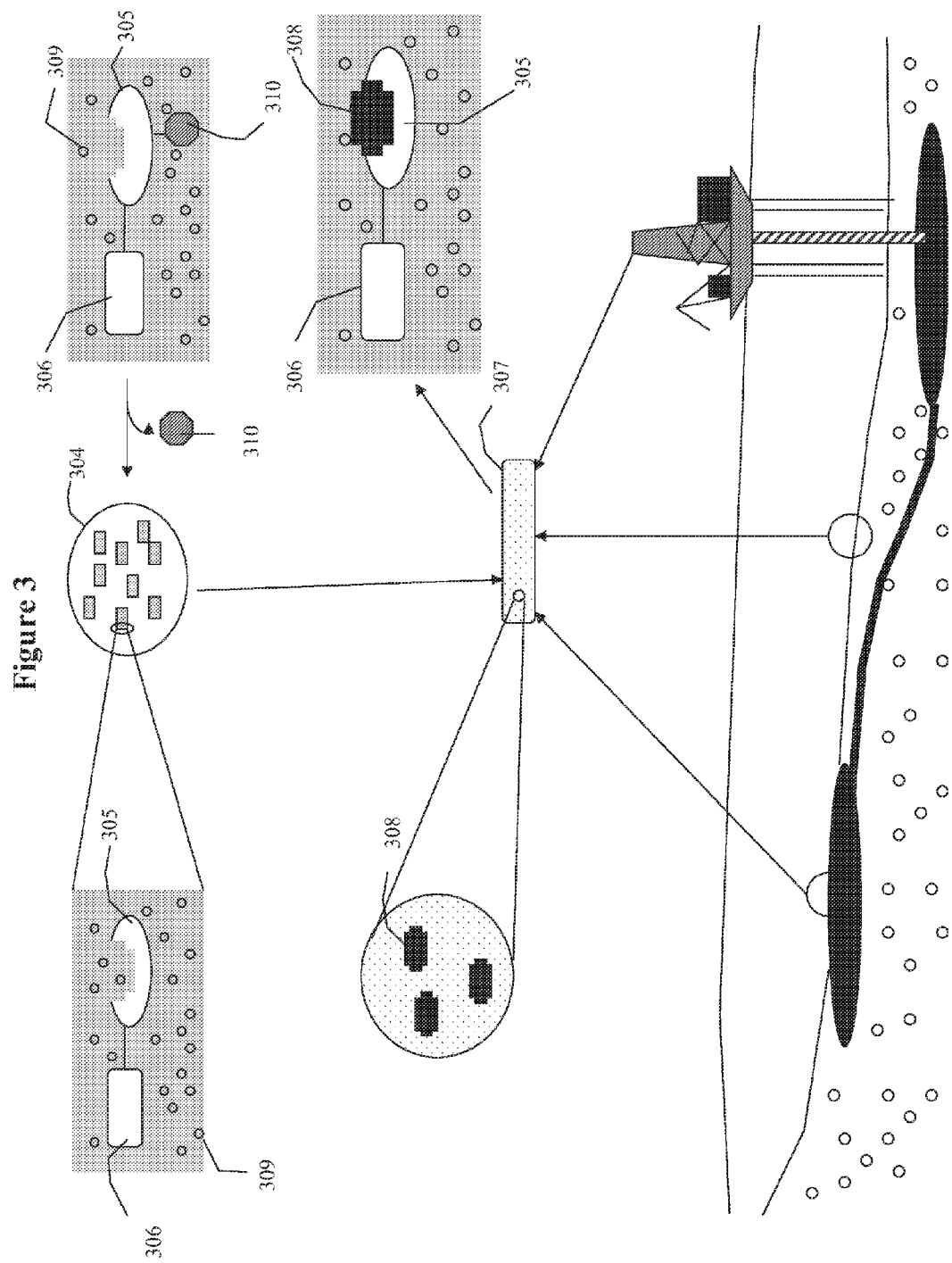

NANOPARTICLE PROBES, METHODS, AND SYSTEMS FOR USE THEREOF

CROSS-REFERENCE TO RELATED APPLICATION

This application is the National Stage of International Application No. PCT/US2012/045574, that published as WO 2013/062640, filed 5 Jul. 2012, which claims the benefit of U.S. Provisional Application No. 61/549,618, filed 20 Oct. 2011, entitled NANOPARTICLE PROBES, METHODS, AND SYSTEMS FOR USE THEREOF, each of which is incorporated by reference herein, in its entirety, for all purposes.

FIELD OF THE INVENTION

Embodiments of the disclosure relate to the field of petroleum geology. More particularly, embodiments of the disclosure relate to identifying geological hydrocarbon materials.

BACKGROUND

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

The exploration for and discovery of new oil reserves has become increasingly challenging and costly. Untapped reserves tend to be more difficult to identify and evaluate, and very often are located subsea, which further increases complexity and cost of the exploration and discovery of such reserves. Successful, efficient, and cost effective identification and evaluation of hydrocarbon-bearing reservoirs is therefore very desirable.

In exploration, seep detection has become an important tool to identify potential hydrocarbon resources in the subsurface. Oil and gas accumulations often leak hydrocarbons including methane, ethane, propane, butane, naphthalene, and benzene. These hydrocarbons may migrate toward the surface through a variety of pathways that result in seeps discharging hydrocarbons to the surface. These seeps are thus surface expressions of subsurface geological phenomena. In some instances, seeps may be laterally displaced at some distance away from the accumulation from which they originate. Seeps may be classified as macroseeps and microseeps, which differ in hydrocarbon volumes or areal extent over which the seep discharges.

Active hydrocarbon systems are often identified by sampling surface expressions of subsurface geological phenomena, such as faults or fracture zones, that are likely hydrocarbon conduits. Currently discharging seeps ("active" seeps) or paleo-seeps are typically identified by seismic survey interpretations and may also be located with ship-board, side-scan sonar, or other techniques during the survey. Usually only one core sample is taken at each feature. The core samples are usually several feet in length and are collected below the surface or below the water-sediment interface. The cores are then typically transported to land-based laboratories for analysis using fluorescence and standard petroleum geochemistry techniques. The costs of seep surveys are accordingly very high and may be in the range of a million US dollars for a forty sample survey. Due to the prohibitive costs, sampling density tends to be quite low. Accordingly there exists a need for identifying currently discharging seeps indicative of active hydrocarbon systems.

Once a likely site for the hydrocarbon accumulation has been established, an exploration well is drilled. Upon the drilling of the well, evaluation of the subsurface geology surrounding the well is typically achieved through indirect methods such as mud logging and well-based geophysical techniques such as electrical conductance, acoustics, and radioactive decay.

While formation evaluation techniques such as well logging remain the standard for the petroleum industry, these techniques are less than robust where challenging conditions exist. For instance, there may be cases where the presence of hydrocarbons, fluid type (gas, oil, and/or water), and proportion of hydrocarbon to water in the pore spaces are ambiguous even after formation evaluation. For example, carbonate reservoirs, thin-bedded clastic rocks, and wells containing very fresh water are particularly troublesome to evaluate using current standard techniques. Also, current formation evaluation techniques tend to be unable to distinguish moveable from immovable oil, particularly where the oil is biodegraded or severely altered. Contamination or invasion into the formation by hydrocarbon-based drilling fluids is yet another complication that makes distinguishing the natural hydrocarbon composition and quality using standard logging or geochemical methods much more difficult. Even further, when wells are drilled and only water is located in the potential reservoir unit, the standard formation evaluation techniques do not provide a reliable way to determine whether there are hydrocarbons in an updip or adjacent position (such as across a fault).

Accordingly there exists a substantial need for reliable, reproducible, efficient, robust, real-time and cost-effective means for identifying and evaluating hydrocarbon-bearing formations. In particular, there exists a substantial need for improving the efficacy and reliability of seep surveys, and to reduce the cost of seep surveys.

SUMMARY

In some embodiments, the present disclosure relates to a method of identifying geological materials of interest comprising (i) providing a nanoprobe composition comprising one or more nanoprobes; wherein the nanoprobe comprises (a) at least one tag; and (b) at least one signal generator; (ii) introducing the nanoprobe composition to a geological material; and (iii) detecting the presence of a signal generated by the signal generator on association of the tag with a target.

In other embodiments, the present disclosure relates to a nanoprobe composition comprising one or more nanoprobes, wherein the nanoprobe comprises (a) at least one tag capable of associating with a target found in geological materials; and (b) at least one signal generator capable of generating a signal when the tag associates with the target.

In further embodiments, the present disclosure relates to a method of evaluating a geological material comprising (a) providing a first nanoprobe; wherein the first nanoprobe comprises (i) one or more tags that associate with a target; and (ii) one or more first signal generators; (b) providing a second nanoprobe; wherein the second nanoprobe comprises (i) one or more tags that associate with water; and (ii) one or more second signal generators; (c) introducing a nanoprobe composition comprising the first nanoprobe and the second nanoprobe to the geological materials; (d) measuring a first signal; wherein the first signal is generated upon the association of the first nanoprobe with the target; (e) measuring a second signal; wherein the second signal is generated upon the association of the second nanoprobe with water; (f) comparing the first signal to the second signal; and (g) deriving an estimation of the respective proportions of water and target in the geological materials.

In yet other embodiments, the present disclosure relates to a system for the characterization of geological materials comprising (a) a nanoprobe composition comprising one or more nanoprobes; wherein the nanoprobe comprises (i) at least one tag; and (ii) at least one signal generator; and (b) at least one detector capable of detecting a signal generated by the signal generator.

BRIEF DESCRIPTION OF THE DRAWINGS

The foregoing and other advantages of the present disclosure may become apparent upon reviewing the following detailed description and drawings of non-limiting examples of embodiments in which:

FIG. 3 shows representative methods of identifying geologic materials of interest.

DETAILED DESCRIPTION

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the broadest definition persons in the pertinent art have given that term as reflected in at least one printed publication or issued patent.

Embodiments herein relate to identifying and evaluating hydrocarbon-bearing formations using nanoprobes. In particular, embodiments herein relate to nanoprobes useful for detecting geological materials of interest, methods of detecting such geological materials, methods of evaluating such geological materials, and systems for the evaluation of these geological materials. "Geological materials" includes subsurface rock regions, zones or volumes and/or fluids associated therewith, and samples thereof. These geological materials may contain hydrocarbons or be devoid of hydrocarbons. "Geological materials of interest" are those that comprise hydrocarbons. Geological materials of interest may be found, for example, on a sea floor; on an area of sub-aerial land; or in a well bore, in a rock unit, comprising, for example limestone, sandstone, etc. Geological materials of interest may comprise sediments, rocks, or cores or cuttings; hydrocarbon-bearing formations or samples thereof; or alternatively, oil, natural gas, or other fluids that have been obtained from a wellbore.

In some embodiments, the geological materials may be in situ, for example, a test area in a wellbore or a fracture. In other embodiments, the geological materials may be ex situ, for example, conventional cores, drop cores, cuttings, fluid samples, and sediment samples. Some examples of geological materials of interest are shown in FIG. 1.

Figure 1:
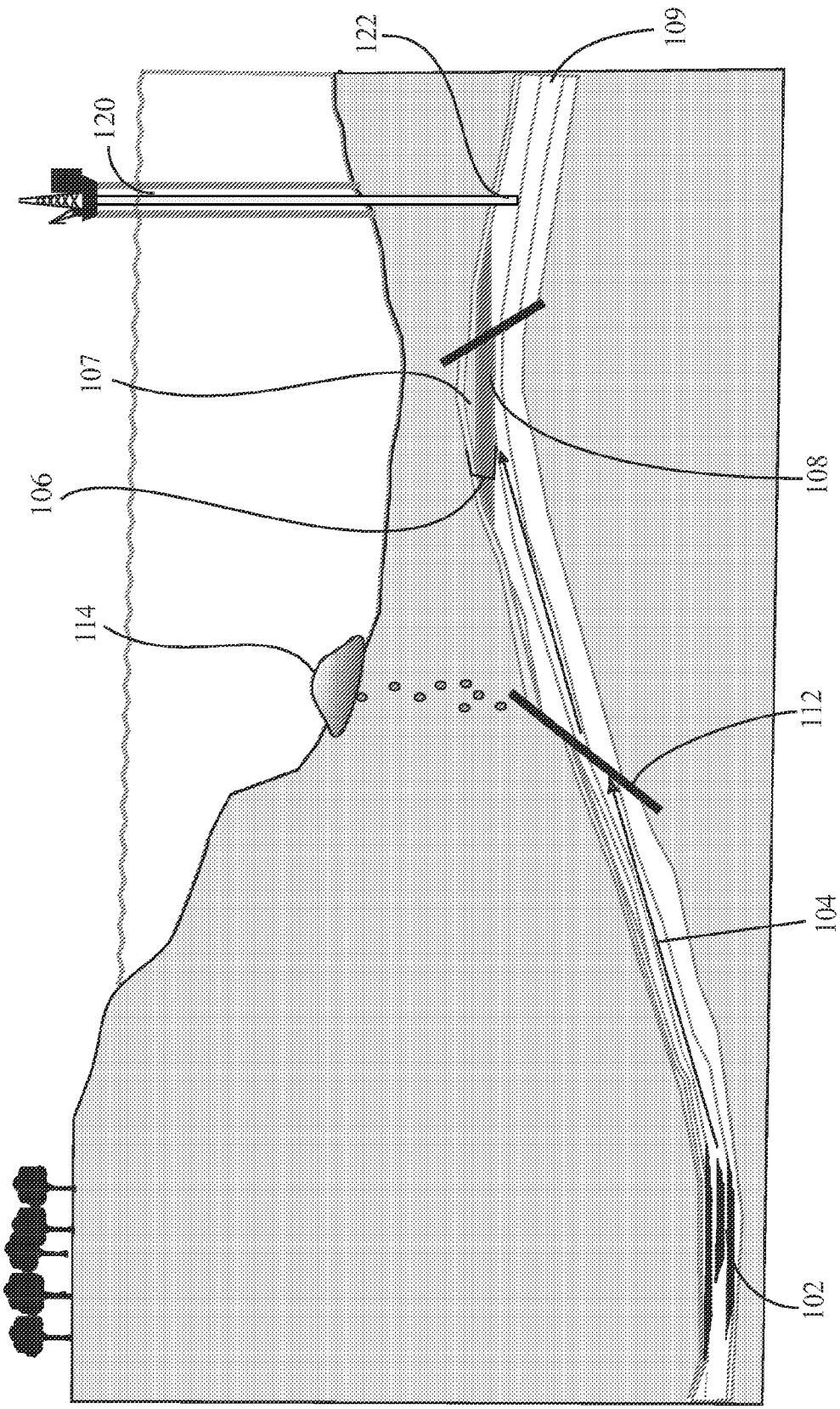
FIG. 1 is a schematic of components of a hydrocarbon system.

FIG. 1 shows a representative hydrocarbon system. "Hydrocarbon system" refers to a system for the formation and production of hydrocarbons. "Hydrocarbons" refers to any number of carbon and hydrogen-containing compounds and/or mixtures of compounds that may originate within subsurface formations, such as in the reservoir thereof. Illustrative, non-exclusive examples of hydrocarbons according to the present disclosure may include petroleum, oil, crude oil, natural gas, tar, bitumen, and/or mixtures of these materials, as well as any other naturally occurring organic compound that may be found within subsurface geologic formations. The terms oil, crude oil, petroleum, and liquid hydrocarbon may all be used interchangeably herein. "Subsurface" includes below the surface of the earth or below the surface of the earth.

Source rock 102 is a sedimentary rock that forms by the conversion of sediments and organic matter via compation or other processes to a more consolidated form during burial. During burial and over time, increases in temperature and pressure cause organic matter transformations resulting in production of hydrocarbons. With increasing pressure hydrocarbons are then expelled from source rocks and travel to zones with lower pressure via migration pathways 104. These hydrocarbons may be stored in reservoir units 106, which typically have higher porosity and permeability than source rocks. If a migration pathway, such as along a fracture or fault zone 112, intersects with the air-sediment or water-sediment interface then a hydrocarbon seep 114 may occur.

For example, when hydrocarbon migration pathways intersect sea bottom sediment surfaces, hydrocarbons and fluids maybe conveyed to the surface, forming readily identifiable surface features (such as a macroseep at a fault). Some hydrocarbons may leak to the sediment surface over a large area with less hydrocarbons released at any one particular location (such microseep). Regardless of seep size and volume conveyed, microbial communities will establish on these surfaces and in the subsurface, where nutrients, fluid properties, temperature and pressure are conducive to their growth and proliferation. Within seeps, large populations of indigenous microorganisms which metabolize these hydrocarbons may become established. Indeed, there are 79 bacterial genera, 9 cyanobacterial genera, 103 fungal genera, and 14 algal genera that are known to degrade or transform hydrocarbons (for more information on such microorganisms, see Head et al., "Marine microorganisms make a meal of oil." Nature Reviews Microbiology, 4 (2006), 173-182, 2008). These microorganisms thrive in environments comprising hydrocarbons. Such microorganisms may include bacteria or Archaea, for example *Pseudomonas* spp., *Beggiatoa* spp. or other proteobacteria, and other similar organisms.

Various microorganisms metabolize specific hydrocarbons. There are greater than 17,000 identified compounds in crude oil including asphaltenes, resins, saturated and aromatic hydrocarbons. Of these compounds, the saturated and aromatic hydrocarbons are typically the most abundant. Microorganisms that digest these saturated and aromatic hydrocarbons are of particular interest because they will most likely be present in larger populations in any given geological material. For example, bacteria such as *Alcanivorax* sp. which metabolize branched chain hydrocarbons, *Cycloclasticus* sp. which metabolize aromatic hydrocarbons, *Polaromonas naphthalenivorans* CJ2 which metabolize naphthalene, and *Burkholderia* sp. strain EBA09 which metabolize benzene may be present in large populations in geological materials comprising hydrocarbons (see Head et al.).

The inventors surmise that the nanoprobes, methods, and systems of the present invention will be useful in identifying the location of active seeps, for example, at or near a water-sediment interface, such as at a sea floor or under ice, or at an air-sediment interface. The nanoprobes, methods, and systems of the present invention may be useful in detecting particular hydrocarbons, particular microorganism DNA and/or RNA, and/or metabolic products of these microorganisms in geological material, in situ or ex situ.

FIG. 1 also shows an offshore well 120 penetrating into a water zone 109 in a formation comprising a reservoir unit containing hydrocarbons. "Formation" means a subsurface region, regardless of size, comprising subsurface sedimentary, metamorphic and/or igneous matter, whether consolidated or unconsolidated, and other subsurface matter, whether in a solid, semi-solid, liquid and/or gaseous state, related to the geological history of the subsurface region. A formation may contain numerous geologic strata of different ages, textures and mineralogic compositions. A formation can refer to a single set of related geologic strata of a specific rock type, or to a whole set of geologic strata of different rock types that contribute to or are encountered in, for example, without limitation, (i) the creation, generation and/or entrapment of hydrocarbons or minerals and (ii) the execution of processes used to extract hydrocarbons or minerals from the subsurface. Although the well shown is offshore, embodiments of the present disclosure are not so limited.

The formations associated with reservoir units may also have a natural gas zone 107 and a crude oil zone 108. Generally, reservoirs may comprise either a natural gas zone 107 or a crude oil zone 108, both, or neither. Because the well penetrates into the water zone 109, the well appears to be predominantly water-bearing (i.e., dry hole 122), even though there is a crude oil zone and a natural gas zone in close proximity. Drilling wells is a very expensive undertaking. Accordingly drilling what appears to be a dry hole could result in the loss of the drilling costs as well as the opportunity costs of lost time.

The water zone 109 may however comprise water-soluble hydrocarbons originating from the nearby crude oil zone 108. For example, these water-soluble hydrocarbons may include organic acids, benzene, toluene, ethyl benzene, and xylene. However, collection of samples that are representative of subsurface conditions, such as from the water zone, tends to be problematic. Very often the act of removal may change the sample's composition and adversely affect the accuracy of the composition analysis. Therefore, the in situ detection of such water soluble compounds would prove very advantageous, allowing real-time, representative, reproducible formation evaluation. The use of the nanoprobes as disclosed herein may advantageously allow the in situ detection of nearby oil zones and/or a gas zone, thereby reducing the risk of a false negative assessment of a drilled well and avoiding the concomitant loss of time and money.

Nanoprobes

Embodiments herein relate to nanoprobes useful for detecting target geological materials and evaluating formations. More specifically, embodiments herein relate to nanoprobe compositions, methods of use, and systems comprising these nanoprobe compositions.

In some embodiments, the present disclosure relates to a nanoprobe composition comprising one or more nanoprobes, wherein the nanoprobe comprises (a) at least one tag capable of associating with a target found in geological materials; and (b) at least one signal generator capable of generating a signal when the tag associates with the target.

A "nanoprobe" is a molecular agent that is used for detecting target molecules. The nanoprobes herein comprise at least one tag and at least one signal generator. In some embodiments, the tag may comprise a signal generator. They are typically sub-micron size. Depending on the application and the identity of the tag and signal generator, the nanoprobe may not necessarily be nanometer scale in size.

The Tag

A "tag" is a component of a nanoprobe that associates with the target. In some embodiments herein, the tag may be a DNA, an RNA, or a hydrocarbon tracer. A "tracer" is a tool for identifying the presence of the target. In some embodiments the tracer is a hydrocarbon tracer useful for identifying the presence of a particular hydrocarbon or class of hydrocarbons. In other embodiments, the tracer is a DNA primer or DNA fragment, useful for identifying an organism or metabolic process of an organism. "Associates" as used in reference to the association between a tag and a target herein, refers to any interaction between the tag and the target that causes a signal to be generated by the signal generator. Examples of such interactions typically comprise electronic, chemical, physical, and/or steric interactions between the tag and the target, such as complementary base pair binding between a DNA or RNA primer and the target DNA or RNA, or a chemical reaction between a hydrocarbon and a hydrocarbon tracer.

Figure 2:
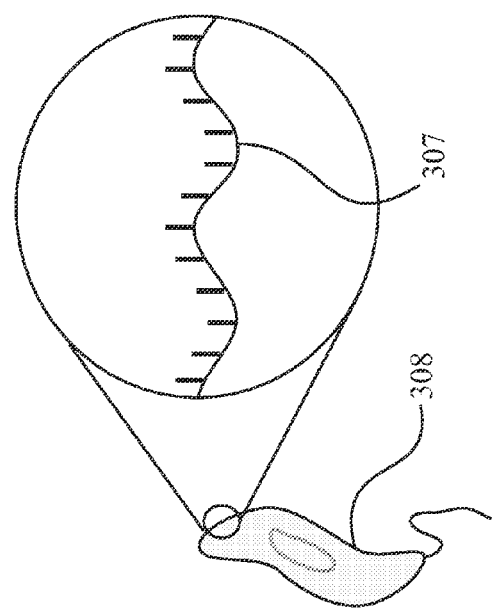
FIG. 2 is a schematic of geomolecular and biomolecular nanoprobes useful herein.
Figure 2:
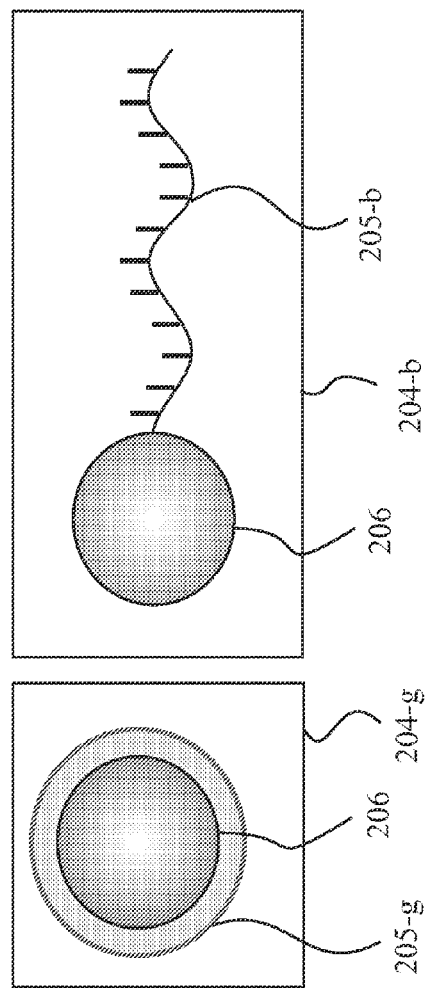

The tag may be biomolecular or geomolecular. FIG. 2 shows representations of geomolecular and biomolecular probes.

Biomolecular tags typically associate with biological targets such as microorganisms, in particular the genetic material, cell wall material, or cell membrane material of such microorganisms. Examples of such biomolecular tags include DNA and RNA primers. Such DNA and RNA primers may be complementary to sections of the microorganism genetic material characteristic of a particular species; and/or sections of the genetic material that encode for a specific metabolic function, such as metabolizing hydrocarbons; or sections of the genetic material that encode for processes making use of the products of this metabolysis, such as sulfate reduction, methanogenesis, and the like. Biomolecular tags may be identified and designed by any means known in the art, such as pyrosequencing-based metagenomics, single cell genomics, or other well known techniques. Biomolecular tags may also be purchased from commercial source, for example Life Technologies Corporation (formerly Invitrogen Corporation, Carlsbad, Calif.).

FIG. 2 shows a microorganism 308 which metabolizes hydrocarbons having a biological target 307 (here genetic material is represented). FIG. 2 also shows a nanoprobe 204-b comprising a signal generator 206 and a biomolecular tag 205-b that is complementary to and will associate with the biological target 307. Accordingly, use of the nanoprobe 204-b will identify the presence of the microorganism 308, which may indicate the direct or nearby presence of hydrocarbons.

Geomolecular tags typically associate with particular hydrocarbons, for example, a hydrocarbon tracer compound that associates with aromatic compounds such as toluene, benzene, ethyl benzene, or xylene. In some embodiments, the geomolecular tags may comprise a functional group that attaches to a functional group of interest in the target. In other embodiments, the geomolecular tag may react the target hydrocarbons. In yet other embodiments, the geomolecular tag may sorb onto the target hydrocarbons. "Sorbing" or "sorption" includes adsorption, chemical adsorption (i.e., chemisorption), absorption, and/or physical adsorption (i.e., physiosorption). In other embodiments, the geomolecular tag may associate with the hydrocarbons by partitioning in the presence of hydrocarbons. "Partitioning" means the relative solubility of a compound in a mixture of two or more immiscible solvents. For example, a compound may partition at the interface of a mixture of a polar and a nonpolar compound, for instance, oil and water. Where the compound is hydrophilic, the compound will be preferentially found in the polar layer and is referred to as having a low partition coefficient. Where the compound is hydrophobic, the compound will preferentially migrate to the nonpolar layer and is referred to as having a high partition coefficient. Amphiphilic compounds may partition at the interface of the oil/water mixture. In some embodiments, the nanoprobe may have two or more tags, alternately three or more tags, and so on.

FIG. 2 further shows a geomolecular probe 204-g which comprises a geomolecular tag 205-g and a signal generator 206. The geomolecular tag may surround or encapsulate the signal generator 206, as shown, or be appended to the signal generator 206.

The tag, whether biomolecular or geomolecular, associates with a target found in the geological material. "Target" means a target of interest with which the tag associates. In some embodiments herein, the target is at least one of hydrocarbons, microorganisms that metabolize hydrocarbons, and compounds produced by the microorganisms, such as metabolic products. In other embodiments, the target is one of genetic material of microorganisms that metabolize the geological material, polysaccharides found on the cell walls of microorganisms that metabolize the geological material, and proteins, lipids or sterols found in the cell membranes of microorganisms that metabolize the geological material. Examples of targets include hydrocarbons such as toluene, benzene, ethyl benzene, and xylene, genetic material of microorganisms, for example *Alcanivorax* spp., and/or metabolic byproducts such as 2-methylbenzyl succinate for toluene (Young and Phelps, 2005, Metabolic biomarkers for monitoring in situ anaerobic hydrocarbon degradation. Environmental Health Perspectives 113 (1): 62-67) and de-methylated hopanes for hopanes (Wenger, Davis, and Isaksen, 2002, Multiple controls on petroleum biodegradation and impact on oil quality, SPE Reservoir Evaluation and Engineering, 5: 375-383).

The Signal Generator

"Signal generator" refers to a molecule that generates a signal when the tag associates with the target. In some embodiments, signal generator is a nanoparticle. A nanoparticle is a very small particle with at least one dimension less than 100 nm. Some examples of nanoparticles include nanopowders, nanoclusters, and nanocrystals. Such nanoparticles are of great scientific interest, particularly in sensory applications, as they have size-dependent properties. A bulk material typically has constant physical properties regardless of its size, but at the nanoscale this is often not the case. Size-dependent properties are observed such as quantum confinement in semiconductor particles, surface plasmon resonance in some metal particles and superparamagnetism in magnetic materials. The properties of materials change as their size approaches the nanoscale and as the percentage of atoms at the surface of a material becomes significant. Accordingly, nanoparticles are of particular importance as signal generators in the present disclosure.

In some embodiments, the signal generator is preferably an inorganic fluorophore. Conventional tracing and imaging technologies in other fields, such as the medical and biological fields, typically use organic dyes as markers or probes. These dyes are susceptible to degradation by photoexcitation, room light, or high temperatures. These organic dyes are therefore not suitable for the high pressure and high temperature conditions of downhole environments. Additionally, such organic tracers or dyes may stick to the well walls or associate indiscriminately with sediments and fail to reach the target.

In some embodiments the nanoparticle is one or more of a silicon nanoparticle, a cadmium selenide nanoparticle, a cadmium sulfide nanoparticle, a quantum dot, a nanoparticle composite, a nanocrystal, and a carbon nanotube. "Quantum dots" are nanometer sized semiconductor materials typically made from semiconductor elements such as silicon or germanium, or semiconductor compounds, such as CdS or CdSe. These nanoparticles may differ in color depending on their size. Quantum dots may also be of interest as signal generators for their other unusual properties including electrical and nonlinear optical properties. Quantum dots can also emit light if excited, with the smaller the dot, the higher the energy of the emitted light. Advantageously, quantum dots do not degrade rapidly and may not stick to other materials found in core samples or in the wellbore.

In particular embodiments, the signal generator is an inorganic fluorophore. In other particular embodiments, the signal generator is at least one of a silicon nanoparticle and a cadmium selenide nanoparticle.

"Signal" relates to any type of signal used to indicate the presence of hydrocarbons or microorganisms that metabolize the geological material. In some embodiments, the intensity of a signal may change on association of the target with the tag. In some embodiments, a signal is generated on association of the tag with the target. In other embodiments, in the absence of a suitable complementary target, no signal will be generated. In such embodiments, the absence of a signal suggests that the geological material does not contain hydrocarbons. In yet other embodiments, in the presence of a suitable complementary target, a signal is quenched. In some embodiments, the signal generated is at least one of audible, sonar, acoustic, visible, infrared, electrical, and fluorescent signals. In particular embodiments, the signal may be a change of color or fluorescence. For example, silicon nanoparticles may take on different colors depending on the size of the nanoparticle. Accordingly, the free nanoprobe may have a different color or intensity of color than the tag-target association.

Depending on the design and application of the nanoprobe composition, the signals produced by the signal generators of the nanoprobes may take the form of one or more of a variety of detectable signals, such as infrared, visible, ultraviolet (UV), acoustic, electric, radiation, and the like. Detection methods will vary depending on the signal type; for example, a visible color change may be immediately discernable by visual observation or by a spectrometer, while fluorescence might be detectable by fluorimetric techniques known to one of skill in the art, such as by using a fluorimeter.

The signals from the signal generators may be analyzed in any convenient manner. Some such signals might be of mainly binary interest, for example, because they indicate that a particular hydrocarbon either is or is not present in the geological materials. In other embodiments, the presence of the signal and its magnitude or intensity may be useful. For example, the presence of the signal may indicate that a particular hydrocarbon is present in the geological material and the intensity of the same or another signal may give an indication of approximately how much of the hydrocarbon is present.

Analysis techniques common in the art are useful for the interpretation of the signals. For example a calibration curve may be used to correlate the fluorescence signature or signatures to the hydrocarbon concentration, and/or to the abundance of micro-organisms, in the sample. In some cases, suitable corrections may be needed to compensate for biasing factors such as, for example, contamination from marine organisms living in the surface sediments, from marine organic matter recently deposited on the sediment surface, or from other hydrocarbons not associated with a subsurface petroleum deposit.

Some embodiments herein relate to a nanoprobe composition, wherein the nanoprobe composition further comprises a reagent. As used herein "reagent" refers to a formulation which allows the nanoprobe to be more effectively delivered to the geological material to be tested. In some embodiments, the reagent may comprise a fluid, which allows pouring, spraying, aerial dispersion, or dissolution into or onto the geological material. In particular embodiments, the reagent is selected from the group consisting of drilling fluids, water, brine, organic solvents, and a mixture thereof. In other embodiments, the reagent comprises a solid, thereby allowing sprinkling of the nanoprobe composition onto the geological material to be tested, or allowing dissolving of the nanoprobe in a fluid to be injected into the geological material, or allowing timed release of the nanoprobe downhole. In particular embodiments, the reagent also may amplify the signal by any means known in the art.

In other embodiments, the present disclosure relates to a system for the characterization of geological materials comprising (a) a nanoprobe composition comprising one or more nanoprobes; wherein the nanoprobe comprises (i) at least one tag; and (ii) at least one signal generator; and (b) at least one detector capable of detecting a signal generated by the signal generator.

The change in a signal, presence of a signal, or absence of a signal is preferably detectable by some means known in the art. In some embodiments, detecting the signal comprises using one or more of a UV-Vis spectrometer, IR spectrometer, a fluorimeter, a Raman spectrometer, and a sonar detector. In some embodiments, the signal may be detected visually or audially by an observer.

Methods of Identifying & Evaluating Geological Materials of Interest

Some embodiments herein relate to a wellsite or lab-based use of nanoprobes for the rapid assessment of the presence of hydrocarbons. The assessment may be ex situ or in situ. In embodiments where the assessment is in situ, the nanoprobes may be introduced into the wellbore for the purpose of formation evaluation or alternatively, may be contacted with a the surface of a seep. In particular embodiments, the nanoprobe composition may be injected into a wellbore or sprayed onto a seep. The ability to conduct real-time, in situ formation evaluation or seep evaluation provides cost savings and improves the efficiency of the exploration and drilling processes.

In embodiments where the assessment is ex situ, the nanoprobes may be contacted with a sample of the geological material. The sample may comprise well-derived rock samples such as conventional cores, sidewall cores, cuttings, or fluids encountered in the wellbore or a seep sample such as from drop cores. In particular embodiments, the nanoprobe composition may be sprayed on a sample cutting at the wellsite and the presence of a signal immediately determined. The ability to conduct accurate, representative ex situ analysis at the wellsite may present appreciable cost savings over conventional techniques.

In some embodiments, the present disclosure relates to a method of identifying geological materials of interest comprising (i) providing a nanoprobe composition comprising one or more nanoprobes; wherein the nanoprobe comprises (a) at least one tag; and (b) at least one signal generator; (ii) introducing the nanoprobes to a geological material; and (iii) detecting the presence of a signal generated by the signal generator on association of the tag with a target.

FIG. 3 shows a flowchart of representative methods of identifying geological materials of interest. Geological materials 307 may be sampled in situ or ex situ from seeps, wells, or from interesting geological features. Geological materials 307 may include, for example, a sediment sample, or perhaps a fluid sample in or over a surface feature associated with a hydrocarbon seep (such as a pockmark or mound), or in or over a sediment where no obvious surface feature exists, such as in a micro-seep. The geological materials of interest comprise a target 308.

The geological materials 307 are contacted with a nanoprobe composition 304. The nanoprobe composition comprises nanoprobes. The nanoprobes comprise a signal generator 306 and a tag 305. The tag 305 is designed to interact with the target 308. On interaction with the target, the signal generator produces a signal. Some signal generators might be of the type that do not produce a signal until activated, for example by an ultraviolet light or a radio signal, while others might automatically produce a signal. For those types of signal generators, an activation process is used. In some applications, activation can take the form of detaching an agent 310 that prevents the signal generator from emitting a signal, or quenches the signal emitted from the nanoprobe. Although the agent 310 is shown as being attached to the tag 305, one of skill in the art would appreciate that the agent may be attached to the nanoprobe at any position or by any means known in the art.

For some applications, the nanoprobe composition 304 may further comprise a reagent 309 which would allow ease of application to the geological material 307. Such a reagent could take the form of, for example, a powder, pellet, solution, or suspension. In some embodiments, it may be appropriate to encase, protect, or otherwise carry the nanoprobe composition in a carrier medium of some kind. The selection of the carrier medium will be affected by the environment in which the nanoprobes are to be applied. For example, the potential adverse effects of sea water and/or pressure on the nanoprobes' durability may prompt the selection of a carrier medium that allows the nanoprobe to resist salinity and/or pressure to a certain critical amount or for a certain time. For purposes of this disclosure and the claims below, such carrier media should be considered as reagents.

In other embodiments, the nanoprobe composition may be part of an article. In some embodiments, the article is at least one of a sheet, film, net, or mesh. Such articles may be laid down on top of (or otherwise applied to) the geological material. This may allow ease of application of the nanoprobe composition, for example to subsea seeps.

In some embodiments, nanoprobe composition may be injected into the geological material, as opposed to being applied to the surface of the sample. In such embodiments, the signal generators desirably emit suitable signals (for example, acoustic or radiation signals) that can be detected even when the signal generators are beneath the surface of the sample.

In other embodiments, the nanoprobe composition may be introduced to formation or seep in situ. Any apparatus for introducing such compositions that are known in the art may be used. Additionally, adaptations of apparatuses known in the art for introduction into a formation or seep are also within the scope of the present disclosure. For example, some variation of the coiled-tube apparatus shown in FIGS. 1A and 1B of Pelham et al., "Evaluation of Hydrocarbon Reservoirs and Associated Fluids Using Biological Tags and Real-Time PCR," U.S. Patent Application Serial No. 2010/0015612 A1 may be adapted for this purpose. In particular embodiments, the nanoprobe composition is mixed into a fluid solution or suspension, for example in drilling fluid or secondary-injection fluid, the fluid is pumped into a well bore or into a natural- or artificially-created fracture. This would permit detection of the direction and extent of induced or natural fractures during hydraulic fracturing of conventional and unconventional (e.g., tight gas, tight oil, shale gas) reservoirs. Very advantageously, signal production and detection can take place down-hole, that is, in the well, without having to first extract the nanoprobe composition from the well for analysis.

In yet other embodiments, a nanoprobe composition may be attached, by any means known in the art, to a delivery probe, which could be lowered into a well bore or otherwise made to traverse the geological material. In particular embodiments, the delivery probe might be attached to a suitable self-propelled vehicle, such as an automated underwater vehicle (AUV). In such embodiments, the self-propelled vehicle may make a first pass over the sample area to deliver quantities of nanoprobes, then on a second pass, attempt to detect any signals that might be generated by the signal generators.

When the nanoprobe compositions are introduced to the geological material, the tags will bind or otherwise associate with any targets in the sample that are accessible to the tags. Upon association, the signal generator may emit a signal.

The signal may be detected by detectors that analyze the signal received. For example, after induced fracturing, activation of "passive" nanoparticles having a known frequency acoustic response, could be detected with geophones used in microseismic surveying (generally, passive listening for seismically-generated signals such as for example acoustic signals). This signal could distinguish between the extent of natural cracks (assessed using microseismic geophones) and the extent of proppant (material such as sand, used to keep a fracture open) which correlates to the extent of effective, open induced fractures.

In particular embodiments, the present disclosure allows for the assessment of hydrocarbon saturation, that is, the proportion of hydrocarbon to water in the pore spaces. In such embodiments, the present disclosure relates to a method of evaluating a geological material comprising (a) providing a first nanoprobe; wherein the first nanoprobe comprises (i) one or more tags that associate with a target; and (ii) one or more first signal generators; (b) providing a second nanoprobe; wherein the second nanoprobe comprises (i) one or more tags that associate with water; and (ii) one or more second signal generators; (c) introducing a nanoprobe composition comprising the first nanoprobe and the second nanoprobe to the geological materials; (d) measuring a first signal; wherein the first signal is generated upon the association of the first nanoprobe with the target; (e) measuring a second signal; wherein the second signal is generated upon the association of the second nanoprobe with water; (f) comparing the first signal to the second signal; and (g) deriving an estimation of the respective proportions of water and target in the geological materials.

Applications

Embodiments herein may be used in a variety of ways to detect and evaluate geological materials. Embodiments disclosed herein are suitable for both land-based applications and subsea applications. The nanoprobes, methods, and systems disclosed herein also present several advantages, some of which are discussed below. A significant advantage of these nanoprobes, methods, and systems is that in many cases they can be applied in the field in real time. This allows workers to make sampling and/or strategical decisions on site, without the delays typically associated with shipping one or more samples to a remote laboratory for analysis.

In some embodiments, the nanoprobes, methods, and systems disclosed herein may be used to indicate the locations of accumulations or migrations of hydrocarbons, for example, downhole, by in situ or ex situ assessment. In some embodiments, the nanoprobes, methods, and systems disclosed herein may be used to indicate the location of hydrocarbon seeps, for example at or near a water-sediment interface (such as at a sea or lake floor, or under ice) or at an air-sediment interface.

In other embodiments, the nanoprobes, methods, and systems disclosed herein may be used to detect the location of hydrocarbons leaks in the event of unplanned releases.

In yet other embodiments, the nanoprobes, methods, and systems disclosed herein may be used to evaluate a dry hole for the presence of water soluble hydrocarbons that may be indicative of a nearby reservoir, for example in an up-dip or across a fault.

In other embodiments, the nanoprobes, methods, and systems disclosed herein may be used to detect hydrocarbons in carbonate reservoirs, thin-bedded reservoirs, tight-rock reservoirs (those of low porosity and permeability), and reservoirs containing very fresh water. These reservoirs generally pose difficulties in accurate assessment using conventional techniques. In such geological areas, hard surface conditions (such as carbonate hard grounds and the like) may make it difficult or impossible to perform drop-core sampling. In those areas, however, hydrocarbon compounds of interest, and/or microbial organisms that metabolize such compounds, might be present on the surface. The nanoprobes, methods, and systems disclosed herein are advantageous because they may used in situ and can provide real-time reliable feedback as to whether these areas are likely to be suitable candidates for exploration.

In some embodiments, the nanoprobes, methods, and systems disclosed herein may be used to differentiate between moveable and immovable oil. Immoveable oil is typically viscous and otherwise difficult to extract, for example due to being biodegraded or otherwise severely altered. The nanoprobes, methods, and systems disclosed herein may be used to determine the flowability of the oil in situ, thereby providing information about the nature of the hydrocarbons within the reservoir.

In yet other embodiments, the nanoprobes, methods, and systems disclosed herein may be used to indicate the locations of areas having different hydrocarbon accumulation types are in contact with each other, or in contact with water accumulation, for example, oil-water, oil-gas, and gas-water contact areas.

In other embodiments, the nanoprobes, methods, and systems disclosed herein may be used to distinguish in-place hydrocarbons from those introduced by drilling fluids or generated by drilling artifacts such as drill-bit metamorphism.

Some additional advantages of the present disclosure are discussed below. Seismic exploration often entails performing comparatively less expensive two-dimensional (2D) surveys of a geological area to identify likely candidates for further exploration (that is, specific areas thought to contain oil, natural gas, etc.). The identified likely candidates are then subjected to more expensive three-dimensional (3D) surveys. The nanoprobes, methods, and systems disclosed herein may be used to indicate described herein could be used to prescreen selected areas, based on the 2D survey results, to assess where hydrocarbons are thought likely to be. This would allow prioritizing specific areas for the more expensive 3D surveys, thus possibly reducing the economic risk and enhancing the cost-effectiveness of the 3D surveys.

A specific advantage of the nanoprobes, methods, and systems is that each nanoprobe contains both a tag and a generator in a single package. As a result, the nanoprobes can begin producing usable signals directly from contact with the target (in some embodiments, after being activated). This is particularly advantageous, especially in field applications, not to have to do any additional processing of the geological material, such as extraction of sediments and extensive preparation for quantitative polymerase chain reaction techniques.

In other embodiments herein:

1. A method of identifying geological materials of interest comprising:
(i) providing a nanoprobe composition comprising one or more nanoprobes;
wherein the nanoprobe comprises:
   (a) at least one tag (preferably the tag is one or more of a hydrocarbon, a DNA, and a RNA tracer); and
   (b) at least one signal generator (preferably the signal generator is a nanoparticle (preferably the nanoparticle is one or more of a silicon nanoparticle, a cadmium selenide nanoparticle, a cadmium-sulfide nanoparticle, a quantum dot, a nanoparticle composite, a nanocrystal, and a carbon nanotube); preferably the signal generator is an inorganic fluorophore;
(ii) introducing the nanoprobes (preferably introducing the nanoprobes is ex-situ or in-situ; preferably when the introduction is in-situ, introducing comprises injecting the nanoprobes downhole; preferably when the introduction is ex-situ, introducing comprises any of spraying, sprinkling, dusting, and contacting the geological material) to a geological material (preferably when the introduction is in-situ, the geological material is subsurface or in a seep; preferably when the introduction is ex-situ, the geological material is a sample (preferably the sample comprises any of conventional cores, drop cores, cuttings, sidewall cores, fluids, and sediment)); and
(iii) detecting (preferably detecting comprises using one or more of a UV-Vis spectrometer, IR spectrometer, a fluorimeter, a Raman spectrometer, and a sonar detector) the presence of a signal generated (preferably the signal generated is at least one of an audible, a sonar, an acoustic, a visible, and a fluorescent signal) by the signal generator on association of the tag with a target (preferably the target is at least one of hydrocarbons, microorganisms that metabolize the geological material, and compounds produced by the microorganisms that metabolize the geological material; preferably the target is one of genetic material of microorganisms that metabolize the geological material, polysaccharides found on the cell walls of microorganisms that metabolize the geological material, and proteins found in the cell membranes of microorganisms that metabolize the geological material).

2. The method of paragraph 1, wherein association of the tag with the target comprises one or more of sorbing, partitioning, anionic bonding, hydrogen bonding, covalent bonding, and adhesion.

3. The method of paragraphs 1 and 2, wherein the tag is a DNA or RNA primer and the target is genetic material of the microorganisms that metabolize the geological material.

4. A nanoprobe composition useful in the method of paragraphs 1 to 3 comprising one or more nanoprobes, wherein the nanoprobe comprises:
   (a) at least one tag (preferably the tag is one or more of a hydrocarbon, a DNA, and a RNA tracer);
   (b) at least one signal generator (preferably the signal generator is a nanoparticle (the nanoparticle is one or more of a silicon nanoparticle, a cadmium selenide nanoparticle, a cadmium-sulfide nanoparticle, a quantum dot, a nanoparticle composite, a nanocrystal, and a carbon nanotube); preferably the signal generator is an inorganic fluorophore); and
   (c) optionally, a reagent (preferably the reagent is selected from the group consisting of drilling fluids, water, brine, organic solvents, and a mixture thereof).

5. An article (preferably the article is at least one of a sheet, film, net, or mesh) comprising the nanoprobe composition of paragraph 4 and useful in the methods of paragraphs 1 to 3.

6. A method of evaluating geological materials using the nanoprobe composition of paragraph 4 or the article of paragraph 5 comprising:
   (a) providing a first nanoprobe; wherein the first nanoprobe comprises:
      (i) one or more tags that associate with a target compound (preferably the tag of the first nanoprobe is hydrophobic); and
      (ii) one or more signal generators;
   (b) providing a second nanoprobe; wherein the second nanoprobe comprises:
      (i) one or more tags that associate with water (preferably the tag of the second nanoprobe is hydrophilic); and
      (ii) one or more signal generators;
   (c) introducing a nanoprobe composition comprising the first nanoprobe and the second nanoprobe to the geological materials (optionally the nanoprobe composition further comprises a reagent (preferably the reagent is selected from the group consisting of drilling fluids, water, brine, organic solvents, and a mixture thereof));
   (d) measuring a first signal; wherein the first signal is generated upon the association of the first nanoprobe with the target compound;
   (e) measuring a second signal; wherein the second signal is generated upon the association of the second nanoprobe with water;
   (f) comparing the first signal to the second signal; and
   (g) deriving an estimation of the respective proportions of water and target in the geological materials.

7. The method of paragraph 6, wherein the first and/or second signal generated is at least one of an audible, a sonar, an acoustic, a visible, and a fluorescent signal.

8. A system for the characterization of geological materials comprising:
   (i) the nanoprobe composition of paragraph 4 or the article of paragraph 5;
   (ii) at least one detector capable of detecting a signal generated by the signal generator; and
   (iii) optionally, a means for introducing the nanoprobe composition downhole.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A method of identifying geological materials of interest comprising:
   (i) providing a nanoprobe composition comprising one or more nanoprobes;
   wherein the nanoprobe comprises:
      (a) at least one tag; and
      (b) at least one signal generator;
   (ii) introducing the nanoprobes to a geological material; and
   (iii) detecting the presence of a signal generated by the signal generator on association of the tag with a target.

2. The method of claim 1, wherein introducing the nanoprobes to the geological material occurs ex situ or in situ.

3. The method of claim 2, wherein the ex situ introduction of the nanoprobes to the geological material comprises contacting the nanoprobes with a sample.

4. The method of claim 1, wherein the in situ introduction of the nanoprobes to a geological material comprises injecting the nanoprobes into a subsurface formation or contacting the nanoprobes with a seep.

5. The method of claim 1, wherein the target is at least one of hydrocarbons, microorganisms that metabolize the geological material, and compounds produced by the microorganisms that metabolize the geological material.

6. The method of claim 1, wherein the target is one of genetic material of microorganisms that metabolize the geological material, polysaccharides found on the cell walls of microorganisms that metabolize the geological material, and proteins or sterols found in the cell membranes of microorganisms that metabolize the geological material.

7. The method of claim 1, wherein the tag is one or more of a hydrocarbon, a DNA, and a RNA tracer.

8. The method of claim 1, wherein the signal generator is a nanoparticle.

9. The method of claim 1, wherein the signal generator is an inorganic fluorophore.

10. The method of claim 8, wherein the nanoparticle is one or more of a silicon nanoparticle, a cadmium selenide nanoparticle, a cadmium-sulfide nanoparticle, a quantum dot, a nanoparticle composite, a nanocrystal, and a carbon nanotube.

11. The method of claim 1, wherein association of the tag with the target comprises one or more of sorbing, partitioning, anionic bonding, hydrogen bonding, covalent bonding, and adhesion.

12. The method of claim 1, wherein the signal generated is at least one of an audible, a sonar, an acoustic, a visible, and a fluorescent signal.

13. The method of claim 1, wherein the tag is a DNA or RNA primer and the target is genetic material of the microorganisms that metabolize the geological material.

14. The method of claim 1, wherein detecting further comprises using one or more of a UV-Vis spectrometer, IR spectrometer, a fluorimeter, a Raman spectrometer, and a sonar detector.

15. A nanoprobe composition comprising:
   one or more nanoprobes, wherein the nanoprobe comprises:
      (a) at least one tag capable of associating with a target found in geological materials; and
      (b) at least one signal generator capable of generating a signal when the tag associates with the target.

16. The nanoprobe composition of claim 15, further comprising a reagent.

17. The nanoprobe composition of claim 16, wherein the reagent is selected from the group consisting of drilling fluids, water, brine, organic solvents, and a mixture thereof.

18. The nanoprobe composition of claim 15, wherein the tag is one or more of a hydrocarbon, a DNA, and a RNA tracer.

19. The nanoprobe composition of claim 15, wherein the signal generator is a nanoparticle.

20. The nanoprobe composition of claim 15, wherein the signal generator is an inorganic fluorophore.

21. The nanoprobe composition of claim 18, wherein the nanoparticle is one or more of a silicon nanoparticle, a cadmium selenide nanoparticle, a cadmium-sulfide nanoparticle, a quantum dot, a nanoparticle composite, a nanocrystal, and a carbon nanotube.

22. The nanoprobe composition of claim 15, wherein the signal generated is at least one of an audible, a sonar, an acoustic, a visible, and a fluorescent signal.

23. An article comprising the nanoprobe composition of claim 15.

24. The article of claim 23, wherein the article is at least one of a sheet, film, net, or mesh.

25. A method of evaluating a geological material comprising:
   (a) providing a first nanoprobe;
   wherein the first nanoprobe comprises:
      (i) one or more tags that associate with a target; and
      (ii) one or more first signal generators;
   (b) providing a second nanoprobe;
   wherein the second nanoprobe comprises:
      (i) one or more tags that associate with water; and
      (ii) one or more second signal generators;
   (c) introducing a nanoprobe composition comprising the first nanoprobe and the second nanoprobe to the geological materials;
   (d) measuring the first signal;
   wherein the first signal is generated upon the association of the first nanoprobe with the target;
   (e) measuring the second signal;
   wherein the second signal is generated upon the association of the second nanoprobe with water;
   (f) comparing the first signal to the second signal; and
   (g) deriving an estimation of the respective proportions of water and target in the geological materials.

26. The method of claim 25, wherein the tag of the second nanoprobe is hydrophilic.

27. The method of claim 25, wherein the tag of the first nanoprobe is hydrophobic.

28. The method of claim 25, wherein the first and/or second signal generated is at least one of an audible, a sonar, an acoustic, a visible, and a fluorescent signal.

29. The method of claim 25, wherein the nanoprobe composition further comprises a reagent.

30. The method of claim 25, wherein the reagent is selected from the group consisting of drilling fluids, water, brine, organic solvents, and a mixture thereof.

31. A system for the characterization of geological materials comprising:
   (a) a nanoprobe composition comprising one or more nanoprobes;
   wherein the nanoprobe comprises:
      (i) at least one tag; and
      (ii) at least one signal generator; and
   (b) at least one detector capable of detecting a signal generated by the signal generator.

32. The system of claim 31, further comprising a means for introducing the nanoprobe composition downhole.

33. The system of claim 31, wherein the nanoprobe composition further comprises a reagent.

34. The system of claim 33, wherein the reagent is selected from the group consisting of drilling fluids, water, brine, organic solvents, and a mixture thereof.

35. The system of claim 31, wherein the nanoprobe composition is provided in the form of a sheet, film, net, or mesh.

* * * * *